(12) United States Patent
Garman

(10) Patent No.: US 7,060,446 B1
(45) Date of Patent: Jun. 13, 2006

(54) DEVICE COMPRISING A MICROFABRICATED DIFFUSION CHAMBER

(75) Inventor: Andrew J Garman, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/763,827

(22) PCT Filed: Oct. 11, 1999

(86) PCT No.: PCT/GB99/03374

§ 371 (c)(1),
(2), (4) Date: Apr. 23, 2001

(87) PCT Pub. No.: WO00/22434

PCT Pub. Date: Apr. 20, 2000

(30) Foreign Application Priority Data

Oct. 13, 1998 (GB) .............................. 9822242

(51) Int. Cl.
*G01N 33/53* (2006.01)

(52) U.S. Cl. .................. 435/7.1; 435/286.5; 435/287.2; 422/58; 422/68.1; 422/81; 422/82; 422/145; 73/53.01

(58) Field of Classification Search .................. 422/58, 422/68.1, 81, 82, 119, 145, 256; 435/286.5, 435/287.2, 7.1; 73/53.01; 210/634; 436/52
See application file for complete search history.

(56) References Cited

U.S. PATENT DOCUMENTS

| 4,737,268 | A | * | 4/1988 | Giddings et al. | 209/12.2 |
| 5,716,852 | A | * | 2/1998 | Yager et al. | 436/172 |
| 5,932,100 | A | * | 8/1999 | Yager et al. | 210/634 |
| 5,961,832 | A | * | 10/1999 | Shaw et al. | 210/634 |
| 5,971,158 | A | * | 10/1999 | Yager et al. | 209/155 |
| 6,171,865 | B1 | * | 1/2001 | Weigl et al. | 436/52 |
| 6,297,061 | B1 | * | 10/2001 | Wu et al. | 436/518 |

FOREIGN PATENT DOCUMENTS

| WO | 97/00442 | 1/1997 |
| WO | 97/47390 | 12/1997 |

* cited by examiner

*Primary Examiner*—Long V. Le
*Assistant Examiner*—Gary Counts
(74) *Attorney, Agent, or Firm*—Nixon & Vanderhye

(57) ABSTRACT

Assay device which is able to detect molecules which inhibit the binding of a ligand to a receptor using extremely small quantities of ligand and receptor sample. Such devices are useful in the discovery of molecules which may modulate the activity of biologically important target molecules. The device comprises a microfabricated diffusion chamber into which is introduced in mixture of a test compound, a receptor and a ligand for the receptor. Test compounds which can prevent binding of the ligand to the receptor are identified by detecting the presence of ligand outside the area of introduction of the mixture in the diffusion chamber.

5 Claims, 4 Drawing Sheets

DEVICE COMPRISING A MICROFABRICATED DIFFUSION CHAMBER

Disclosed is an assay device which is able to detect molecules which inhibit the binding of a ligand to a receptor using extremely small quantities of ligand and receptor sample. Such devices are useful in the discovery of molecules that may modulate the activity of biologically important target molecules.

BACKGROUND OF THE INVENTION

Currently the pace of change in techniques and tools for discovery of biologically active molecules is increasing with the ability of combinatorial chemistry and multi-parallel synthesis (MPS) to rapidly provide large numbers of diverse molecules to test for biological activity. In addition the mapping and sequencing of the genomes of many plants, animals and parasites, including the human genome, is already providing a growing number of new targets which may be used in biological tests. In the future it is to be expected that the number of biological targets is to grow even further. It is estimated that in the last 100 years of research only 400 human drug targets have been discovered whilst the human genome project when completed at the scheduled time of 2005 will have sequenced at least 100,000 genes, many of which will code for important biological targets for drug therapy.

However, synthetic techniques such as MPS and combinatorial chemistry provide relatively small sample sizes, for example in the microgram range. The limited sample sizes currently produced are not large enough to supply more than a few biological tests before the supply is exhausted. Therefore, resynthesis is required in order to restock the chemical library.

Currently there is an enormous range of in vitro assay techniques used for biological tests. Generally an in vitro biological test involves exposing the isolated biological target to the compound under investigation and measuring interference with the normal binding of the biological target to its ligand. Such tests are typically run on standard 96 well plates and require a minimum sample size of biological target of around 0.1 ml and a minimum amount of a sample size of compound of around 1 µg.

As well as supplies of the test compound running out, supplies of biological target molecules also may be quickly depleted. It is an expensive and tedious task to have to express, isolate and purify the biological target from the biological source.

Therefore, there is a need to find simple, sensitive, high-throughput approaches to the identification of compounds inhibiting ligands binding to biologically important target molecules for use in the pharmaceutical and agrochemical industry. Such a system should use small sample sizes and be amenable to operation by a machine. In particular, miniaturised approaches operating on the picolitre/nanolitre/microlitre scale are particularly desirable, because of the large cost savings and potential for very high throughput. So far there are very few approaches that will work satisfactorily at this scale. One such approach, fluorescence correlation spectroscopy, which is based on differences in diffusion coefficient measured by fluorescence in femtolitre interrogation volume is inherently slow because it measures only small numbers of molecules.

Microfabrication techniques are generally known in the art using tools developed by the semiconductor industry to miniturise electronics, and it is possible to fabricate intricate fluid systems with channel sizes as small as a micron. These devices can be mass-produced inexpensively and are expected to soon be in widespread use for simple analytical tests. See, e.g., Ramsey, J. M. et al. (1995), "Microfabricated chemical measurement Systems," Nature Medicine 1:1093–1096; and Harrison, D. J. et al. (1993), "Micromachining a minaturized capillary electrophoresis-based chemical analysis system on a chip," Science 261:895–897.

Miniaturisation of laboratory techniques is not a simple matter of reducing their size. At small scales different effects become important, rendering some processes inefficient and others useless. It is difficult to replicate smaller versions of some devices because of material or process limitations. For these reasons it is necessary to develop new methods for performing common laboratory tasks on the microscale.

Devices made by micromachining planar substrates have been made and used for chemical separation, analysis, and sensing. See, e.g., Manz, A. et al. (1994), "Electroosmotic pumping and electrophoretic separations for miniaturized chemical analysis system," J. Micromech. Microeng. 4: 257–265. In addition devices have been proposed for preparative, anayltical and diagnostic methods which bring two streams of fluid in laminar flow together which allows molecules to diffuse from one stream to the next, examples are proposed in WO9612541, WO9700442 and U.S. Pat. No. 5,716,852.

SUMMARY OF THE INVENTION

We have found that microfabricated devices can be used in studying the binding of test compounds to biological targets, for instance in a binding assay (testing the ability of a test compound to bind a biological target) or a competition assay (testing the ability of a test compound to interfere with the binding of a biological target to a ligand of the biological target). Such microfabricated assays are based on differences in diffusion between the ligand or the test compound bound to a biological target (hereinafter called "the receptor") and ligand or test compound that is not bound to the receptor.

In its simplest form the microfabricated assay has a liquid containing diffusion chamber within which a limited area, the "diffusion region", into which is introduced a "mixture" comprising a receptor, a test compound, and, optionally, a ligand, which is known ligand for the receptor, the "mixture". If the test compound binds the receptor, or inhibits the binding of the ligand, if present, to the receptor, then the unbound ligand or test compound will diffuse to areas of the diffusion chamber outside the diffusion region significantly faster than ligand or test compound bound to the receptor. Diffusion of unbound ligand/test compound is much more rapid than for ligand/test compound which is bound to the receptor since there is a difference in molecular weight between the unbound ligand/test compound and the ligand/test compound receptor complex and, therefore, a difference in the speed of diffusion.

Alternatively the device and method of the invention may be used for determining whether the test compound will bind the receptor either in the presence or absence of a ligand for the receptor. The test compounds are, preferably, labelled and the extent of binding to the receptor is determined by the amount of slower diffusing bound compound and/or the amount of faster diffusing free compound present outside the diffusion region. In this alternative feature the "mixture" contains the test compound and the receptor.

The cost of microfabricating such devices is low so many of these diffusion chambers may be produced in parallel in a single use disposable array for simultaneous analysis of many test compounds. Alternatively such devices may be reused.

Accordingly we present as a first feature of the invention a microfabricated binding assay device comprising:
(1) a microfabricated diffusion chamber,
(2) a diffusion region within the microfabricated diffusion chamber, and
(3) at least one inlet for introducing liquid into the microfabricated diffusion chamber and for introducing into the diffusion region a mixture comprising a test compound, a receptor and, optionally, a ligand, such that in use the ability of the compound to prevent the binding of the ligand, if present, to the receptor, or the ability of the test compound to bind the receptor, is determined by reference to the diffusion of the test compound, the receptor or the ligand out of the diffusion region.

We present as a further feature of the invention a method for determining in a microfabricated device the ability of a test compound to either interfere with the binding of a ligand to a receptor or to bind with a receptor, which method comprises:
(1) introducing liquid into a microfabricated diffusion chamber,
(2) introducing a mixture comprising a test compound, a receptor and, optionally, a ligand into a diffusion region of the liquid filled microfabricated diffusion chamber, the volume of the diffusion region being smaller than that of the diffusion chamber, and
(3) detecting the diffusion of the test compound, the receptor or the ligand out of the diffusion region.

It will be understood that in the above method steps (1) and (2) may be reversed, or occur simultaneously. Preferably the diffusion of the ligand in step (3) is detected. Preferably the ligand or test compound is labelled. Ideally the test compound, ligand, if present, and receptor are introduced as solutions, in individual or combined solutions.

The diffusion chamber may be any convenient shape, such that the liquid and the mixture in the diffusion region are brought together without mixing. The maximum dimension of the diffusion chamber is up to 500 µm, preferably up to 200 µm. The minimum dimension is at least 2 µm, preferably at least 5 µm.

The diffusion region is an area of the diffusion chamber sufficiently large that differential diffusion of bound from unbound ligand, or test compound, can be determined.

There may also be a separate inlet for the introduction of liquid into the diffusion chamber, and a separate inlet for introducing the mixture, or different inlets for introducing each component of the mixture, or combinations thereof, into the diffusion region.

In an alternative feature of the invention one of the components of the mixture may be introduced into the whole of diffusion chamber, and thereby also the diffusion region, and the remaining component(s) of the mixture added just to the diffusion region. For example, the receptor is introduced into the whole of the diffusion chamber and the test compound and, optionally, the ligand are introduced just to the diffusion region.

In addition to an inlet there may also be an outlet for removing the liquid and mixture from the diffusion chamber to waste. Preferably the flow is continuous such that there is formed a continual stream of liquid flowing from the inlet to the outlet through the diffusion chamber, thus being formed is "a microfabricated conduit". This allows for sequential introduction of different test compounds into the diffusion region of the same diffusion chamber, and thereby continual serial analysis in the same diffusion chamber is achievable. In addition a number of these microfabricated conduits may be placed in parallel and thus a very high throughput of test samples may be achieved. With this feature of the invention it is preferred that the size and dimension of the microfabricated conduit are arranged such that laminar flow of the liquid is created and maintained in the microfabricated conduit, at least between the points where the mixture is introduced and the detection area. In such a device the mixture is introduced only into the diffusion region of the microfabricated conduit, which does not cross the entire cross section of the laminar flow of liquid-see FIG. 4a. As the laminar flow passes through the microfabricated conduit any free ligand or test compound will diffuse out across the remaining cross section of laminar flow outside the diffusion region which does not contain any ligand or test compound—see, for example, FIG. 1.

In an alternative arrangement to the above the mixture is introduced into the entire cross section of the microfabricated conduit and diffusion occurs on either side of the diffusion area—see FIG. 4b. In this feature of the invention laminar flow is not so critical.

We present as a further feature of the invention a microfabricated binding assay device comprising:
(1) an internal surface defining a microfabricated conduit,
(2) a diffusion region within the microfabricated conduit which defines an area which is smaller than the area of cross section, or of the length, of the microfabricated conduit,
(3) the microfabricated conduit having at least one inlet for introducing liquid into the microfabricated conduit and for introducing into the diffusion region a mixture comprising a test compound, a receptor and, optionally, a ligand, and
(4) an outlet for exiting liquid from the microfabricated conduit, such that in use the ability of the compound to prevent the binding of the ligand, if present, to the receptor, or the ability of the test compound to bind the receptor, is determined by reference to the diffusion of the test compound, the receptor or the ligand out of the diffusion region.

We present as a further feature of the invention a method for determining in a microfabricated device the ability of a test compound to either interfere with the binding of a ligand to a receptor or to bind with a receptor, which method comprises:
(1) introducing liquid into the microfabricated conduit,
(2) introducing a mixture comprising a test compound, a receptor and, optionally, a ligand into a diffusion region of the microfabricated conduit, the diffusion region defines an area within the microfabricated conduit which is smaller than the area of cross section, or of the length, of the microfabricated conduit, and
(3) detecting the diffusion of the test compound, or the ligand, if used, out of the diffusion region.

It will be understood that in the above method steps (1) and (2) may be reversed, or occur simultaneously. Preferably the diffusion of the ligand in step (3) is detected. Preferably the ligand or test compound is labelled. Ideally the test compound, ligand and receptor are introduced as solutions, in individual or combined solutions.

BRIEF DESCRIPTION OF THE DRAWINGS

The invention is described in more detail below in the following non-limiting figures.

FIG. 1 is a digrammatical representation of a device of the invention showing the introduction of the three components of the mixture, which are then mixed, and their introduction to a second stream in laminar flow. The movement of unbound test compound or ligand is detected at point 6. Ideally in this device the diffusion area is created to resemble that shown in FIG. 4a.

FIG. 2 is a diagrammatical representation of a device similar to FIG. 1 but where the laminar flow is split at the outlet and the top stream is used to see whether unbound test compound or ligand is present. Ideally in this device the diffusion area is created to resemble that shown in FIG. 4a.

FIGS. 6a and 7a are diagrammatic representations of apparatus for diffusive mixing by the contact of two flows in a mixing channel with allowance for parting product flows.

DETAILED DESCRIPTION OF THE INVENTION

Figure 2:
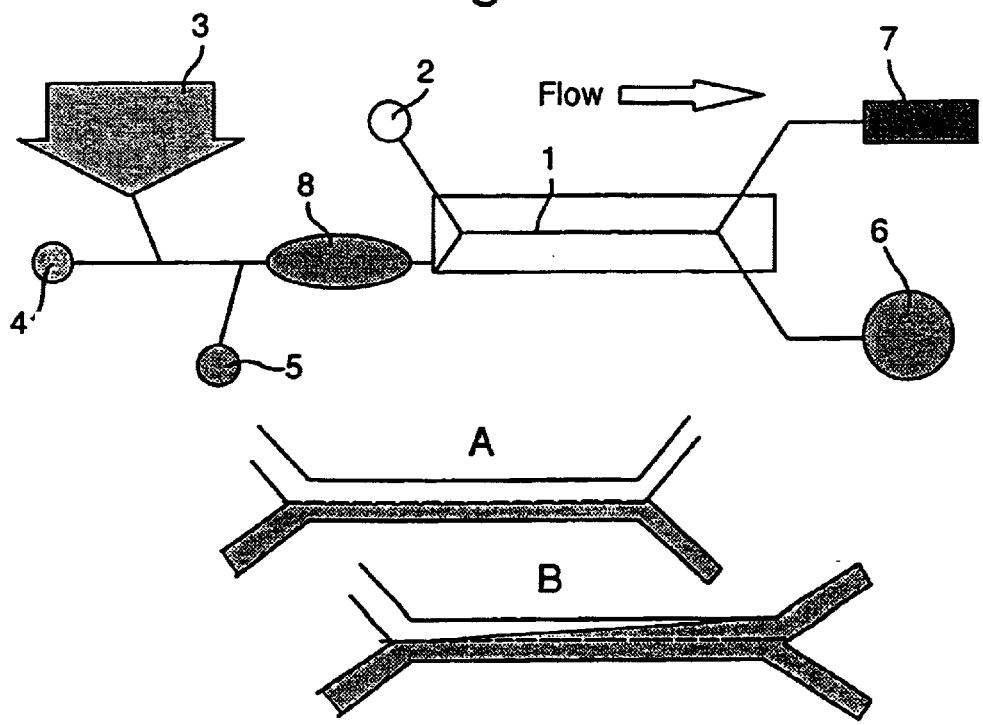

Detection of the presence or absence of ligand or test compound inside or outside the diffusion region may be by external detection means by, for example, detecting changes in an indicator substance present in the liquid of the diffusion chamber, by the use of adsorption spectroscopy or fluorescence, by immunological means, by electrical means, by radioactive means or by the use of any convenient detection system see, for example, FIG. 2. The laminar flow may be separated at the detection area and the separated laminar flow liquid may then be sampled for the presence or absence of unbound ligand or test compound. The concentration of any substance outside the diffusion area may also be measured. Alternatively, simpler detection systems may be employed which monitor the level of fluorescence at a single point (or a few points).

Preferably the liquid streams through the conduit in laminar flow. The term "laminar flow" means stable flow of the liquid through the microfabricated conduit, there being no areas of turbulence. Therefore the presence of test compound or ligand unbound to the receptor outside the diffusion region is entirely due to diffusion and no other effect.

Laminar flow occurs typically in a microfabricated conduit having a depth of no more than 200 µm, and dependant upon the flow rates preferably no more than 100 µm. The depth, or width, of the microfabricated conduit is at least 2 µm, preferably at least 5 µm. Preferably the microfabricated conduit has a constant width with a smooth internal surface. It will be understood that the maintenance of laminar flow is not essential when the diffusion area is orientated as shown, for example, in FIG. 4b. Therefore deeper channels may be used of up to 1 mm, preferably up to 500 µm.

In this is known to disclosure, the term "ligand" refers to any substances of biological or chemical origin, which binds to the receptor to form a complex having a significantly different diffusion rate than unbound ligand. Preferably the ligand is labelled. Preferred labels include fluorescent labels and electrochemically luminescent labels.

In this disclosure, the term "receptor" refers to any substances, preferably of biological origin, which is desired to be screened in a binding test, and that is known to bind to the ligand to form a complex. The complex will have a significantly different diffusion rate than unbound ligand. Examples include enzymes, biological molecules, transcription factors, cell signalling molecules, DNA and RNA. The receptor may be a soluble molecule, e.g. a protein, or an insoluble species, for example a membrane fragment. Optionally the receptor may be a molecule which is normally present on the surface of a cell. Optionally the receptor may be an antibody, in which case the device may be used to carry out an immunoassay. In certain circumstances it may be advantageous to increase the molecular weight of the receptor by conjugation to a macromolecule, particles, liposomes, vesicles and the like. Such conjugation may be either covalent or non-covalent, for example mediated by specific binding pairs such as biotin and streptavidin.

In this disclosure, the term "compound" refers to any substance of biological or chemical origin. Typically compounds of interest are chemically synthesised or naturally isolated organic molecules of molecular weight, in the order of and less than 1000, preferably less than 400. A further use of the invention is to test mixtures of compounds.

In this disclosure, the term "significantly different diffusion" means a diffusion rate different enough to enable the differentiation of diffusion between two molecules to be detected or measured across the point of introduction of the molecules and the detection area. By significant we mean preferably at least 10-fold, more preferably at least 100-fold difference in molecular weight.

In this disclosure, the term "microfabricated" includes devices capable of being fabricated on plastic, glass, silicon wafers or any other material readily available to those practising the art of microfabrication, such as plastic laminate technology. Suitable methods include LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers can be used to accoommodate a plurality of the devices of this invention in a plurality of configurations. A few standard wafer sizes are 3" (7.5 cm), 4" (10 cm), 6" (15 cm), and 8" (20 cm). Application of the principles presented herein using new and emerging microfabrication methods is within the scope and intent of the invention. Microfabricated devices are created through combinations of three essential manufacturing processes: (1) photolithography, the optical process of creating microscopic patterns (2) etching, the process that removes substrate material and (3) deposition, the process whereby materials with a specific function can be coated onto to surface of the substrate. Connections with liquid reservoirs external to the device may be made in accordance with Mourlas N. J. et al. Proceedings of the µTAS'98 Workshop, Kluwer Academic Publishers 27-, and references cited therein.

In this disclosure, the term "liquid" means either an aqueous or non-aqueous liquid, preferably aqueous. In addition the liquid may be buffered and contain any number of molecules essential for the maintained function of the receptor.

Due to the smaller quantities of liquid which are used diffusional distances within the liquid are dramatically lowered allowing for rapid diffusion. However movement of the components of the mixture through the diffusion chamber will equilibrate at different rates. The diffusion rate may be affected by many different factors such as chemical kinetic factors and transport of dissolved material in the solvent by convective, advective, or diffusive processes. Within microfabricated diffusion chambers it is possible to limit convective or advective and in particular turbulent fluid transport so that diffusion is the dominant mode of movement through the liquid. Where diffusive transfer is the limiting factor then the rate of diffusion is related to the length of the path through which the molecule diffuses and the geometry of the liquid body. Diffusive transfer rates will generally be inversely related to the square of the path length.

Typically diffusion coefficients (D) of test compounds or ligands of the size range of interest (MW of a few hundred) will be around $5\times10^{-6}$ cm$^2$s$^{-1}$, diffusion coefficients for a receptor of biological origin will be around $5\times10^{-7}$ cm$^2$s$^{-1}$ (MW of a few hundred thousand) and have diffusive transfer times across a path length (L) which may be derived from expressions of the type $Dt/L^2=0.01$ to 1, where $Dt/L^2=0.01$ approximates to a diffusion front reaching a distance L from source plane, and $Dt/L^2=1$ corresponds to near completion of the diffusive process (concentration gradient across L being nearly eliminated). Approximate times for reaching diffusive equilibration ($Dt/L^{2-1}$) at different path lengths (L), in which the dissolved material must travel, based on $D=5\times10^{-6}$ cm$^2$s$^{-1}$ or $5\times10^{-7}$ cm$^2$s$^{-1}$ are:

|  | MW of a few hundred | MW of a few thousand |
| --- | --- | --- |
| L = 10 μm | t = 0.2 sec | t = 2 sec |
| L = 100 μm | t = 20 sec | t = 200 sec |
| L = 1 mm | t = 0.5 hours | t = 5 hours |
| L = 1 cm | t = 55 hours | t = 550 hours |

About 50% of the diffusive transfer will occur in about a tenth of the above times. Relatively rapid equilibration by diffusion alone will occur within 100 sec when the distance L to the furthest edge of the diffusion chamber from the diffusion region is less than 100 μm. This has an impact on the liquid volume selected, and the diameter of the microfabricated conduit when such a system is being used, depending its geometry, which may be used in static liquid device of the invention, i.e. preferably a liquid volume up to 100 nl, preferably up to 25 nl is used.

As discussed above in the alternative feature of the invention where laminar flow is used in a conduit the approximate maximal diameter of the conduit is 200 μm. Consequently the diffusion path length typically encountered may impose a limitation upon the dimensions of the conduit length to the detection area, taking into account flow rates. Typical flow speeds achievable in microfluidic systems are 0.3 cm/s to 0.03 cm/s, preferably 0.2 to 0.08 cm/s. Therefore on the basis that adequate time is needed for unbound test compound or ligand to diffuse out of the diffusion region but not complexed receptor ligand/test compound then the length of the conduit will range from 0.1 to 3 cm.

It is preferable that the relative concentrations of ligand and receptor in the assay are such that if the test compound were absent little free unbound ligand would be present and, therefore, the presence of any ligand outside the diffusion area is due only to the displacement of bound ligand by the test compound. Preferably the concentration of the receptor should be in excess of that of the compound and or the ligand.

It is preferable that the relative quantities of ligand and receptor entering the diffusion region are such that if the test compound were absent or inactive (capable of preventing binding between ligand and receptor) little of the ligand would remain free unbound by receptor and, therefore the presence of substantial ligand outside the diffusion area is due only to active test compound preventing ligand receptor binding or displacing ligand from receptor.

Prior to the entry of the fluids containing components such as receptors, ligands, and test compounds into the conduit containing the liquid stream and diffusion area, it may be required that two or more component containing fluids are brought together to partially or completely mix or mix and react. This mixing or mixing and reacting may be achieved externally or in channels or conduits linked to or formed together with the conduit containing the liquid stream and diffusion area. Various combinations of channels can be envisaged and in what order they meet before entry into the conduit containing the liquid stream. For example, a compound from a first channel may preferably be mixed with receptor from a second channel prior to the addition of ligand from a third channel. In this way if the compound is inactive ligand will be bound by receptor and when entering the conduit containing the liquid stream and diffusion area will not diffuse as free ligand into the liquid stream. In a preferred alternative the receptor channel and ligand channel may meet before the compound channel, or receptor compound complex may be preformed prior to input into the device. After mixing it may be preferred are put into an "incubation area" this has the advantage that the period for binding of the compound to receptor may be controlled. An incubation area may simply be the length of channel that is between the points where the components of the mixture are introduced and entrance into the diffusion region.

Mixing and reacting of components within channel or conduit systems before entry to the conduit containing the liquid stream and diffusion area may be achieved by a variety of microengineered mixing structures but most appropriately by a combination of a series of channel connections and sections of channel wherein mixing and reaction may occur. As the flow volumes and rates will generally be such that laminar flow conditions will apply, the widths and length of a section where mixing is to occur should be chosen such that diffusive transfer of component species across the direction of flow can achieve the required level of mixing within the transit time through the section. To achieve essentially complete diffusive mixing over a width l in transit time t for a species with diffusion coefficient D the condition $Dt/l^2>1$ should be met. Clearly the time for mixing of different species across the full width of a channel for species of different diffusion coefficients will be set by the lowest diffusion coefficient, usually for the larger more massive species, typically the receptor.

Figure 7A:
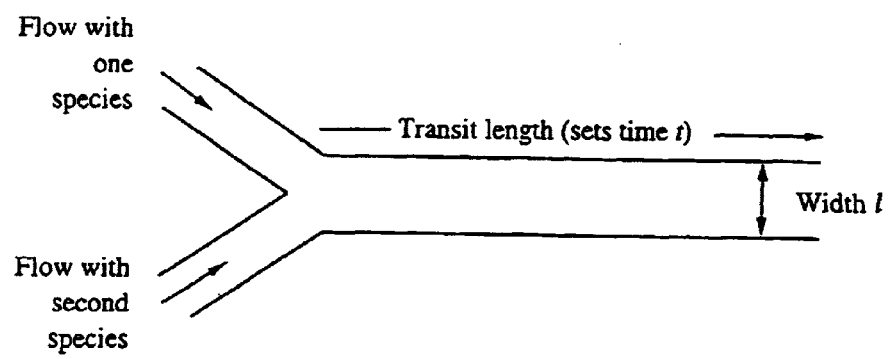

A diagrammatic representation of apparatus for diffusive mixing by the contact of two flows in a mixing channel is shown in FIG. 7a with relevant features indicated.

Where a species, for example a receptor, introduced by one flow into a section where the mixing is to occur is substantially larger and more slowly diffusing than another species, for example a test compound or a ligand, introduced by a second flow into the section where the mixing is to occur, full mixing across the width of a mixing channel can need excessive time and consequent excessive mixing channel length. What may be required is a product stream containing the relevant quantities of fast and slow diffusing species in a well mixed condition, but that product stream need not contain all of the material introduced into the mixing section. It may be adequate to achieve a product stream containing both species with low and high diffusion coefficients by allowing time for the more rapidly diffusing species to have diffused into and across that part of the flow within the mixing section which contains the more slowly diffusing species, and at the end of the mixing section part that product stream from that portion of the flow containing little of the more slowly diffusing species. The transit time for such mixing will be set by the diffusion coefficient of the more rapidly diffusing species and so can be substantially shorter than for full mixing of both input streams.

Figure 7B:
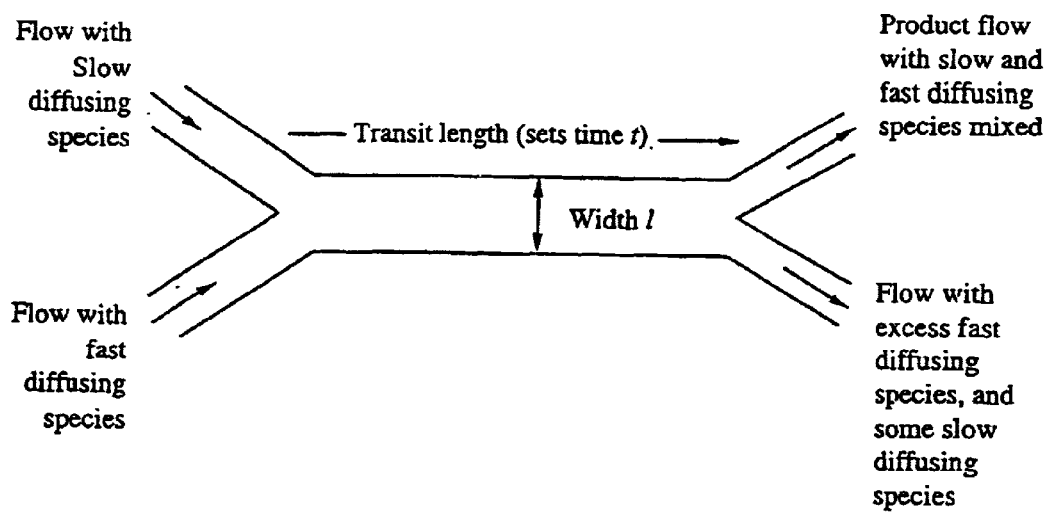

A diagrammatic representation of apparatus for diffusive mixing by the contact of two flows in a mixing channel with allowance for parting product flows is shown in FIG. 7b with relevant features indicated.

The inlet may operate in a pulsed mode, i.e. different compounds are sequentially fed into the system, separated by a buffer "plug" so that the system may operate in a continuous manner. Designs to achieve this will depend on the way that compounds are made available to the system and will be apparent to the microtechnologist of average skill. The compounds entering the device may be from a separation system, such as a chromatography column, attached to the microfabricated device. Thus the device becomes useful for identifying active compounds from a mixture. The above represent further features of the invention.

Further variations on the basic concept will be apparent to the skilled reader and are incorporated in this invention.

The device described here will be capable of high throughput, e.g. tens of determinations per minute. Since the device may be fabricated at a relatively low cost, it will be possible to use several in parallel. One possible configuration will be 96 such devices operating in parallel, with compounds being provided from standard 96 well plates (or higher density plates), at a rate of, for example, one plate of 96 compounds every few seconds.

The device is also capable of immediately giving information about the potency and, optionally, the kinetics of active compounds.

Figure 1:
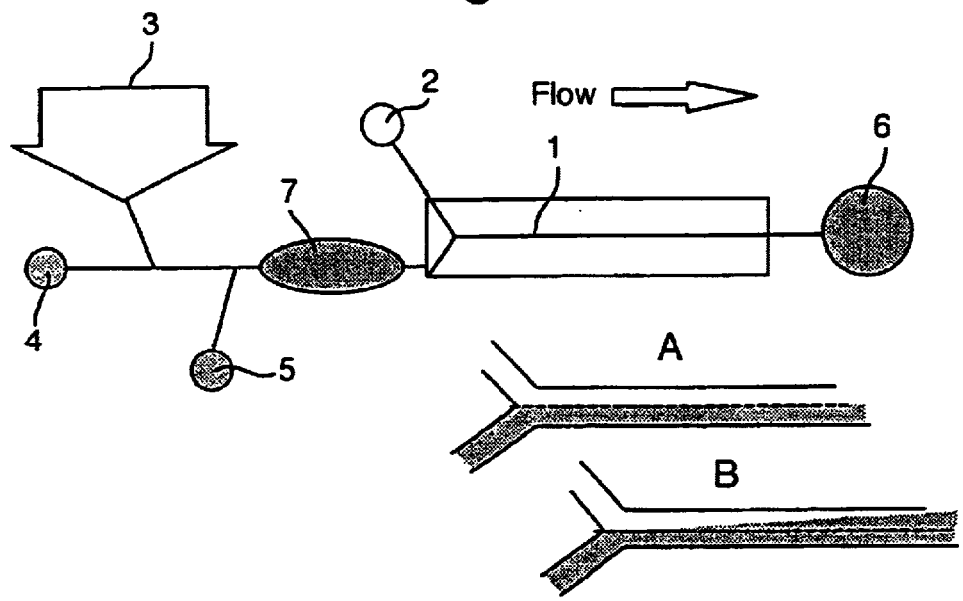

The device is illustrated in the following non-limiting figures:

FIG. 1. Shows a microfabricated conduit 1 having two input channels forming the inlet one of which contains the receptor 4, fluorescent ligand 5 and test compound 3. The three components are mixed in mixer 7. The other channel contains a liquid 2 into which the fluorescent ligand, if unbound, can diffuse. The liquids flow out of the microfabricated conduit 1 into a waste unit 6. Diagram A shows the effect of an inactive compound.

Fluorescent ligand binds to the receptor and the complex remains concentrated in the side of the conduit closest to the inlet channel for flows 3, 4, and 5. Diagram B shows the effect of an active compound in which unbound ligand diffuses across the conduit into the flow of liquid 2.

FIG. 2. Shows an alternative arrangement to FIG. 1. in which the microfabricated conduit is split into two paths. The three components are mixed in mixer 8. The top path may be analysed directly for the presence of fluorescent ligand by a detector 7. Diagram A shows the effect when a compound is inactive. Diagram B shows the effect when the compound is active.

Figure 3:
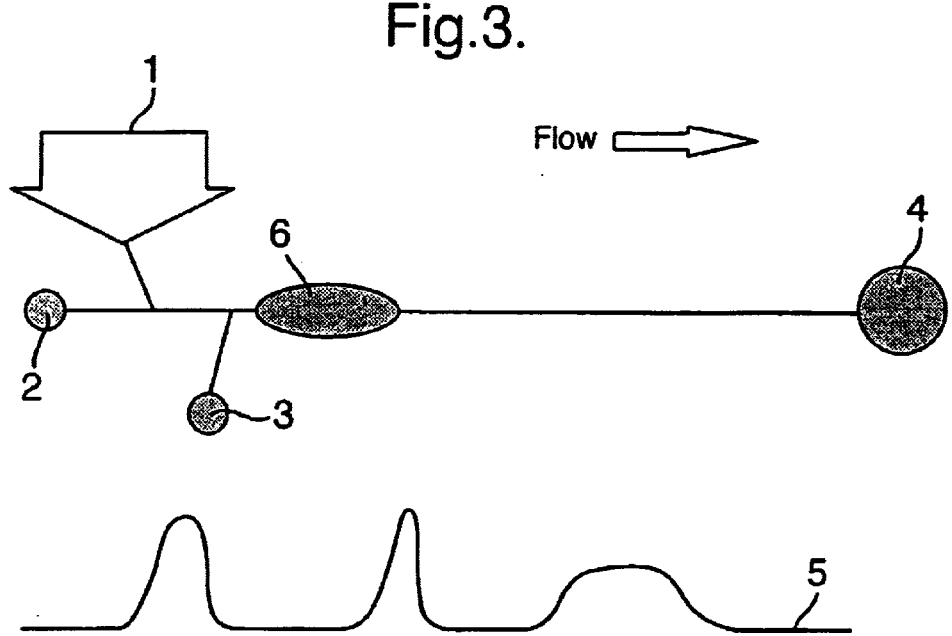
FIG. 3 is a diagrammatic representation of a device similar to that shown in FIG. 1 wherein the detector 4 monitors the labelled component flowing past a single point. Ideally in this device the diffusion area is created to resemble that shown in FIG. 4b and the broader peaks shows that the compound, or ligand, being analysed has diffused out of the diffusion area.

FIG. 3. Shows an alternative arrangement where 1 is an input of compounds, 2 is the receptor, 3 is the labelled ligand where 2 and 3 are also pulsed in synchrony with 1 such that the compound, receptor and labelled ligand all meet. The three components are mixed in mixer 6, 4 is the detector. The readout of the detector is shown at 5 where a labelled ligand concentration is shown against time. The reading shows which compound is interfering with the binding of the ligand to the receptor by the broader peak compared with the neighbouring inactive compounds, indicating diffusion of the labelled ligand away from the diffusion region.

Figure 4:
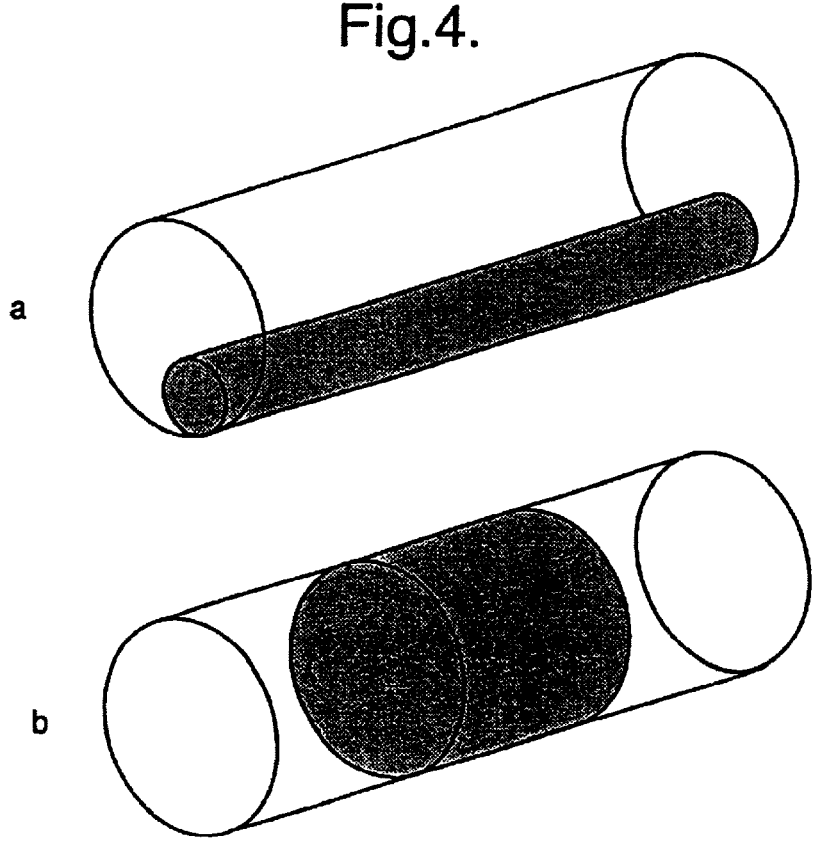
FIGS. 4(a and b) and 5(a and b) are diagrammatical representations of two possible diffusion areas which may be set up within the conduit.

FIG. 4 Shows a diagrammatical representation of two possible orientations of a diffusion area in a conduit.

Figure 5:
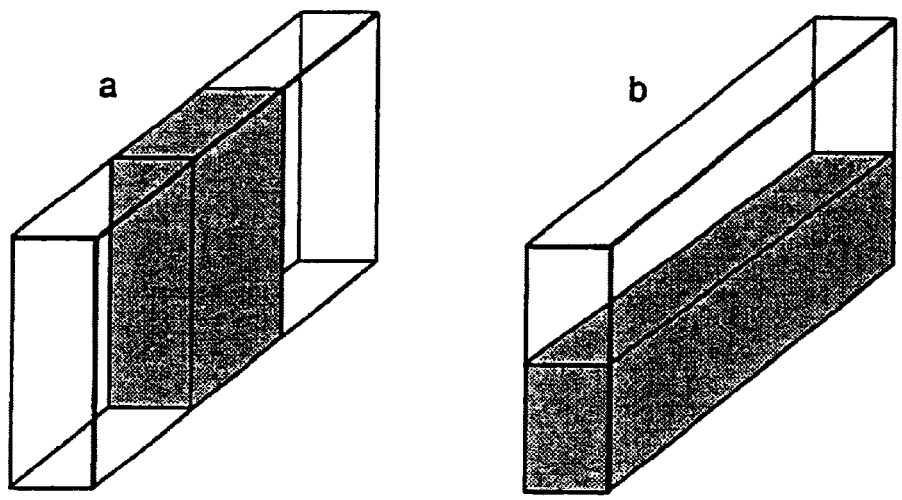
Figure 6:
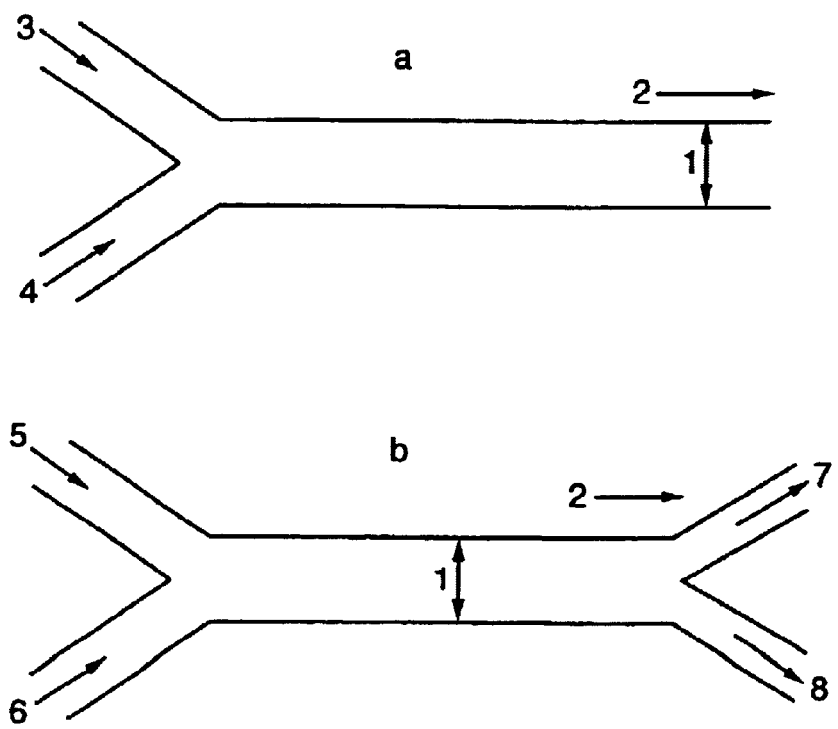
FIGS. 6a and 7a are diagrammatic representations of apparatus for diffusive mixing by the contact of two flows in a mixing channel.

FIG. 5 Shows an alternative diagrammatical representation to FIG. 4 of the same two possible orientations of a diffusion area in a conduit.

If it is considered that the test compound should interact with the ligand first, rather than the receptor, then the ligand and receptor entry ports may be reversed.

Flow may be obtained and controlled in the system by electro-osmosis using electrodes placed at suitable positions on the chip, or by any other convenient means.

In a further aspect, the compound is diluted on the device by the introduction of a buffer flow.

This provides a means for continuously changing the concentration of the compounds introduced, such that a dose-response curve may be acquired and thus a measure of the potency of the compound be obtained. The image analysis system may be designed to quickly identify dose response curves, even when the concentration is varied in a small time scale e.g. a few seconds or less. Optionally the chip control system could "call for" a dose response curve only when it has been determined that the compound in question has a measurable level of activity.

In a further aspect of the system the kinetics of binding of the compound and ligand could be determined by adjusting the flow rates and the incubation times (by for example, introducing loops that extend the length of the channels where the interactions are taking place).

Methods for the manufacture of the devices of the invention may be adapted from those described in WO9612541, WO9700442 and U.S. Pat. No. 5,716,852.

What is claimed is:

1. A microfabricated binding assay device comprising:
   (1) an internal surface defining a microfabricated conduit,
   (2) the microfabricated conduit having at least one inlet for introducing liquid and a mixture comprising a test compound and a receptor or a test compound, a receptor and a ligand,
   (3) means for forming a diffusion region within the microfabricated conduit which extends across the entire cross-section of the conduit, wherein the diffusion region contains the mixture;
   (4) an outlet for exiting liquid from the microfabricated conduit, such that in use the ability of the test compound to prevent the binding of the ligand, if present, to the receptor, or the ability of the test compound to bind the receptor, is determined by reference to the diffusion of the test compound, the receptor or the ligand out of the diffusion region.

2. A device as claimed in claim 1 further comprising a detector for detecting the presence of test compound or ligand.

3. A method for determining in a microfabricated device having a microfabricated conduit the ability of a test compound to either interfere with the binding of a ligand to a receptor or to bind with a receptor, which method comprises:
   (1) introducing liquid into the microfabricated conduit, (2) introducing a mixture comprising a test compound and a receptor or a test compound, a receptor and a ligand into a diffusion region of the microfabricated conduit, the diffusion region extending across the entire cross-section of the conduit, and (3) detecting the diffusion of the test compound, or the ligand, out of the diffusion region.

4. A method as claimed in claim 3 wherein diffusion of the test compound or the ligand is detected on either side of the diffusion region.

5. A device as claimed in claim 1 wherein diffusion out of the diffusion region occurs substantially parallel to the liquid flow.

* * * * *